United States Patent
Horgan et al.

(10) Patent No.: US 10,988,473 B2
(45) Date of Patent: Apr. 27, 2021

(54) PROCESS FOR THE PREPARATION OF (3S,4S)-TETRAHYDROFURAN-3-YL 4-ISOPROPYL-6,7-DIHYDRO-3H-IMIDAZO[4,5-C]PYRIDINE-5(4H)-CARBOXYLATE

(71) Applicant: BENEVOLENTAI CAMBRIDGE LIMITED, London (GB)

(72) Inventors: Viet-Anh Anne Horgan, Cambridge (GB); Olof Haglund, Cambridge (GB); Lee Patient, Cambridge (GB); Edward Savory, Cambridge (GB); Michael Higginbottom, Cambridge (GB); Michael Ashwood, Cambridge (GB)

(73) Assignee: BENEVOLENTAI CAMBRIDGE LIMITED, London (GB)

( * ) Notice: Subject to any disclaimer, the term of this patent is extended or adjusted under 35 U.S.C. 154(b) by 0 days.

(21) Appl. No.: 16/344,608

(22) PCT Filed: Oct. 25, 2017

(86) PCT No.: PCT/GB2017/053218
§ 371 (c)(1),
(2) Date: Apr. 24, 2019

(87) PCT Pub. No.: WO2018/078363
PCT Pub. Date: May 3, 2018

(65) Prior Publication Data
US 2020/0062746 A1  Feb. 27, 2020

(30) Foreign Application Priority Data
Oct. 25, 2016  (GB) ...................................... 1618029

(51) Int. Cl.
*C07D 471/04* (2006.01)

(52) U.S. Cl.
CPC .................................. *C07D 471/04* (2013.01)

(58) Field of Classification Search
CPC ..................................................... C07D 471/04
See application file for complete search history.

(56) References Cited

FOREIGN PATENT DOCUMENTS

| CA | 1 075 240 | 4/1980 |
|----|-----------|--------|
| WO | 2010/031789 | 3/2010 |
| WO | 2016/170351 | 10/2016 |
| WO | 2016/170352 | 10/2016 |
| WO | 2016/170353 | 10/2016 |
| WO | 2017/017414 | 2/2017 |
| WO | 2017/098236 | 6/2017 |

OTHER PUBLICATIONS

International Search Report in International Patent Application No. PCT/GB2017/053218, dated Nov. 28, 2017.
International Preliminary Report on Patentability in International Patent Application No. PCT/GB2017/053218, dated Apr. 30, 2019.

*Primary Examiner* — Noble E Jarrell
(74) *Attorney, Agent, or Firm* — Greenblum & Bernstein P.L.C.

(57) ABSTRACT

The invention relates to an improved process for the synthesis of (3S, 4S)-tetrahydrofuran-3-yl 4-isopropyl-6,7-dihydro-3H-imidazo[4,5-c]pyridine-5(4H)-carboxylate, and pharmaceutically acceptable salts thereof, such as the methanesulphonic acid salt.

20 Claims, No Drawings

PROCESS FOR THE PREPARATION OF (3S,4S)-TETRAHYDROFURAN-3-YL 4-ISOPROPYL-6,7-DIHYDRO-3H-IMIDAZO[4,5-C]PYRIDINE-5(4H)-CARBOXYLATE

FIELD OF THE INVENTION

The present invention relates to an improved process for the synthesis of (3S,4S)-tetrahydrofuran-3-yl 4-isopropyl-6,7-dihydro-3H-imidazo[4,5-c]pyridine-5(4H)-carboxylate, and pharmaceutically acceptable salts thereof, such as the methanesulphonic acid salt.

BACKGROUND

A synthetic process for the preparation of (3S,4S)-tetrahydrofuran-3-yl 4-isopropyl-6,7-dihydro-3H-imidazo[4,5-c]pyridine-5(4H)-carboxylate is known. The synthesis is published in WO2010/031789 (the content of which is herein incorporated by reference in its entirety), where (3S,4S)-tetrahydrofuran-3-yl 4-isopropyl-6,7-dihydro-3H-imidazo[4,5-c]pyridine-5(4H)-carboxylate is Example 16. The known synthetic route is summarised in Scheme 1.

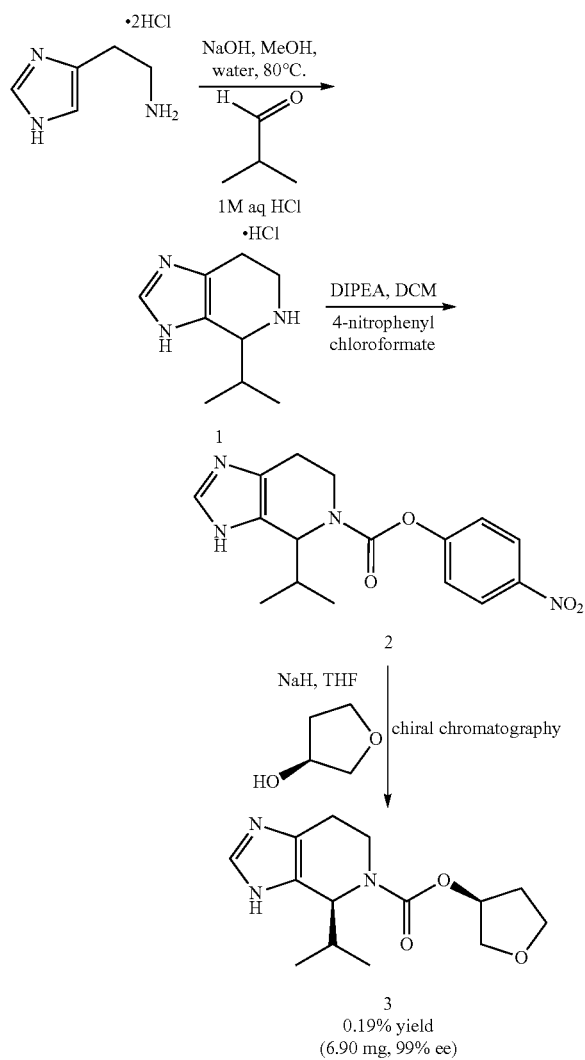

Wherein: NaOH is sodium hydroxide; MeOH is methanol; '1M aq HCl' is a one molar aqueous solution of hydrochloric acid; '.HCl' means the mono hydrochloride salt; DIPEA is N,N-Diisopropylethylamine; DCM is dichloromethane; NaH is sodium hydride, and THF is tetrahydrofuran.

According to the known process, (3S,4S)-tetrahydrofuran-3-yl 4-isopropyl-6,7-dihydro-3H-imidazo[4,5-c]pyridine-5(4H)-carboxylate is prepared in milligram quantities in an overall yield of less than 1%.

(3S,4S)-tetrahydrofuran-3-yl 4-isopropyl-6,7-dihydro-3H-imidazo[4,5-c]pyridine-5(4H)-carboxylate and pharmaceutical salts thereof have shown promising medical utility in the clinic (see EU clinical trials register EudraCT number 2013-001970-33). Therefore an unmet need exists for a reliable and high yielding synthetic process suitable for the large-scale preparation of (3S,4S)-tetrahydrofuran-3-yl 4-isopropyl-6,7-dihydro-3H-imidazo[4,5-c]pyridine-5(4H)-carboxylate and pharmaceutically acceptable salts thereof. Due to its favourable properties such as high stability and low hygroscopicity, the mesylate salt of (3S,4S)-tetrahydrofuran-3-yl 4-isopropyl-6,7-dihydro-3H-imidazo[4,5-c]pyridine-5(4H)-carboxylate is especially interesting. The favourable properties are described in co-pending application PCT/GB2016/051119 (the content of which is herein incorporated by reference in its entirety). Therefore an unmet need exists also for a reliable and high yielding synthetic process suitable for the large-scale preparation of the mesylate salt in particular.

DETAILED DESCRIPTION OF THE INVENTION

Following much research and experimentation, the applicants have made available an improved process for the preparation of (3S,4S)-tetrahydrofuran-3-yl 4-isopropyl-6,7-dihydro-3H-imidazo[4,5-c]pyridine-5(4H)-carboxylate and pharmaceutical salts thereof, particularly the mesylate salt. The new process makes available individual reaction steps having surprising advantages including, but not limited to: high product yields, high product purities, short reaction times, reaction steps having reduced hazards such as reduced toxicity and reduced risk of fire. In addition to improved reaction steps, the applicants also make available novel synthetic intermediate compounds that are straightforward to isolate for example due to improved ease of handling. The applicants also make available novel purification steps, the novel purification steps having the advantage that chromatography is avoided.

In a first aspect, the present invention makes available a process for the preparation of (3S,4S)-tetrahydrofuran-3-yl 4-isopropyl-6,7-dihydro-3H-imidazo[4,5-c]pyridine-5(4H)-carboxylate and pharmaceutically acceptable salts thereof comprising the reaction step of converting histamine (I) to 4-Isopropyl-4,5,6,7-tetrahydro-3H-imidazo[4,5-c]pyridine (II):

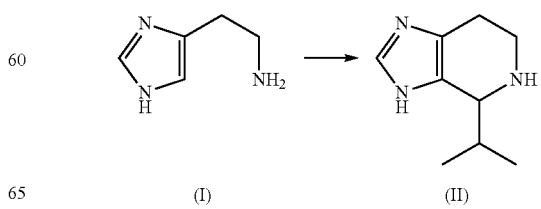

the reaction step comprises isobutyraldehyde (or an equivalent compound which, for example, forms isobutyraldehyde in situ), and wherein
the reaction is maintained at a temperature of from 50 to 100° C. for a period of from 1 to 12 hours. The short reaction time results in a surprisingly high yield and purity of 4-Isopropyl-4,5,6,7-tetrahydro-3H-imidazo[4,5-c]pyridine. In an embodiment the reaction is maintained at a temperature of from 50 to 100° C. for a period of from 2 to 11 hours. In an embodiment the reaction is maintained at a temperature of from 50 to 100° C. for a period of from 3 to 10 hours. In an embodiment the reaction is maintained at a temperature of from 50 to 100° C. for a period of from 4 to 9 hours. In an embodiment the reaction is maintained at a temperature of from 50 to 100° C. for a period of from 5 to 8 hours. In an embodiment the reaction is maintained at a temperature of from 50 to 100° C. for a period of from 5 to 7 hours.

In an embodiment, the reaction is performed in a solvent comprising ethanol, such as substantially pure ethanol. Advantageously, ethanol has reduced toxicity compared to the methanol solvent used in the known synthesis, thus reducing the hazardousness of the reaction step. In an embodiment, the reaction temperature is maintained at a temperature of from 60 to 80° C., such as around 78° C. In an embodiment, the reaction is performed in a solvent comprising ethanol, and the reaction temperature is maintained at reflux (i.e. the boiling temperature of ethanol).

In an embodiment, the process according to the first aspect of the invention comprises the additional step of forming the dihydrochloride salt of 4-Isopropyl-4,5,6,7-tetrahydro-3H-imidazo[4,5-c]pyridine, and in a preferred embodiment the dihydrochloride salt of 4-Isopropyl-4,5,6,7-tetrahydro-3H-imidazo[4,5-c]pyridine is isolated. The dihydrochloride salt may be formed by any method known to the skilled person, such as by addition of acetyl chloride.

Preferably the dihydrochloride salt of 4-Isopropyl-4,5,6,7-tetrahydro-3H-imidazo[4,5-c]pyridine is isolated in a purity of 95% or greater, such as 98% or greater, such as 99% or greater, such as 99.5% or greater. Preferably the isolated 4-Isopropyl-4,5,6,7-tetrahydro-3H-imidazo[4,5-c]pyridine dihydrochloride is obtained in a yield of 80% or greater, such as 90% or greater, such as 95% or greater. Without wishing to be bound by theory, it is believed that the dihydrochloride salt is surprisingly easy to handle, especially when compared to the corresponding monohydrochloride salt used in the known synthesis. This ease of handling is believed to contribute to the high yield and purity of the dihydrochloride salt of 4-Isopropyl-4,5,6,7-tetrahydro-3H-imidazo[4,5-c]pyridine obtained by the above process. Again, without wishing to be bound by theory, it is believed that the use of a solvent comprising ethanol (such as substantially pure ethanol) improves the ease with which the 4-Isopropyl-4,5,6,7-tetrahydro-3H-imidazo[4,5-c]pyridine dihydrochloride is isolated, thus improving the yield and purity.

The histamine starting material can be in any suitable form, such as histamine dihydrochloride which is widely available from commercial sources.

In an embodiment, histamine (or a salt thereof, such as the dihydrochloride salt) is converted to 4-Isopropyl-4,5,6,7-tetrahydro-3H-imidazo[4,5-c]pyridine in a reaction mixture comprising Isobutyraldehyde (or an equivalent thereof); the reaction mixture comprising ethanol as a solvent, wherein the reaction mixture is heated to the temperature of refluxing ethanol (i.e. around 78° C.), and maintained at that temperature for a period of from 3 to 10 hours (such as from 4 to 9 hours), and the resultant 4-Isopropyl-4,5,6,7-tetrahydro-3H-imidazo[4,5-c]pyridine is isolated as the hydrochloride salt.

In a second aspect, the present invention makes available a process for the preparation of (3S,4S)-tetrahydrofuran-3-yl 4-isopropyl-6,7-dihydro-3H-imidazo[4,5-c]pyridine-5(4H)-carboxylate and pharmaceutically acceptable salts thereof using 4-Isopropyl-4,5,6,7-tetrahydro-3H-imidazo[4,5-c]pyridine dihydrochloride. In a preferred embodiment, the 4-Isopropyl-4,5,6,7-tetrahydro-3H-imidazo[4,5-c]pyridine dihydrochloride is isolated as an intermediate. In a preferred embodiment, the 4-Isopropyl-4,5,6,7-tetrahydro-3H-imidazo[4,5-c]pyridine dihydrochloride is isolated from a solution of 4-Isopropyl-4,5,6,7-tetrahydro-3H-imidazo[4,5-c]pyridine in ethanol. Related to the second aspect, the present invention makes available the use of 4-Isopropyl-4,5,6,7-tetrahydro-3H-imidazo[4,5-c]pyridine dihydrochloride in a process for the preparation of (3S,4S)-tetrahydrofuran-3-yl 4-isopropyl-6,7-dihydro-3H-imidazo[4,5-c]pyridine-5(4H)-carboxylate and pharmaceutically acceptable salts thereof. In a preferred embodiment, the 4-Isopropyl-4,5,6,7-tetrahydro-3H-imidazo[4,5-c]pyridine dihydrochloride is isolated as an intermediate. In an embodiment, the pharmaceutically acceptable salt is the mesylate salt.

In a third aspect, the present invention makes available a process for the preparation of (3S,4S)-tetrahydrofuran-3-yl 4-isopropyl-6,7-dihydro-3H-imidazo[4,5-c]pyridine-5(4H)-carboxylate and pharmaceutically acceptable salts thereof comprising the reaction step of coupling 4-Isopropyl-4,5,6,7-tetrahydro-3H-imidazo[4,5-c]pyridine (II) and (S)-(+)-3-hydroxytetrahydrofuran (III) using a coupling agent to form (3S)-Tetrahydrofuran-3-yl 4-isopropyl-6,7-dihydro-3H-imidazo[4,5-c]pyridine-5(4H)-carboxylate (IV):

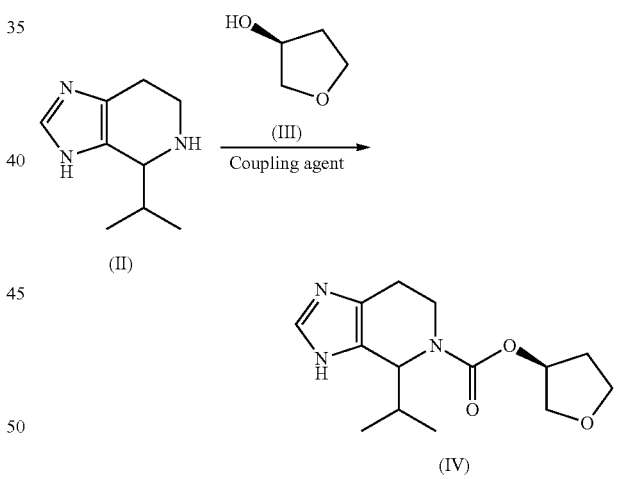

characterised in that the coupling agent is N,N-Disuccinimidyl carbonate.

The use of N,N-Disuccinimidyl carbonate as coupling agent results in a surprisingly high yield of (3S)-Tetrahydrofuran-3-yl 4-isopropyl-6,7-dihydro-3H-imidazo[4,5-c]pyridine-5(4H)-carboxylate, especially when compared to the use of the known coupling agent 4-nitrophenyl chloroformate. In an embodiment (3S)-Tetrahydrofuran-3-yl 4-isopropyl-6,7-dihydro-3H-imidazo[4,5-c]pyridine-5(4H)-carboxylate is obtained in a yield of 70% or greater, such as 75% or greater.

The use of N,N-Disuccinimidyl carbonate as coupling agent results in surprisingly pure (3S)-Tetrahydrofuran-3-yl 4-isopropyl-6,7-dihydro-3H-imidazo[4,5-c]pyridine-5(4H)- carboxylate, especially when compared to the purity of (3S)-Tetrahydrofuran-3-yl 4-isopropyl-6,7-dihydro-3H-imidazo[4,5-c]pyridine-5(4H)-carboxylate when obtained in the known reaction using 4-nitrophenyl chloroformate as coupling agent. In an embodiment, (3S)-Tetrahydrofuran-3-yl 4-isopropyl-6,7-dihydro-3H-imidazo[4,5-c]pyridine-5(4H)-carboxylate is obtained in a purity of 80% or greater, such as 85% or greater.

In an embodiment, the reaction is performed in dichloromethane as a solvent.

In an embodiment, the reaction comprises triethylamine, which acts as a base. The coupling conditions of the present invention are advantageously less hazardous that the known coupling conditions because the highly flammable reagent sodium hydride is avoided. Furthermore, N,N-Disuccinimidyl carbonate has advantageously reduced toxicity, especially compared to 4-nitrophenyl chloroformate which is known to be a severe irritant to skin and eyes. A further advantage over the known coupling conditions is that the potentially carcinogenic 4-nitrophenyl by product from the use of 4-nitrophenyl chloroformate is avoided.

The present invention also makes available (3S)-Tetrahydrofuran-3-yl 4-isopropyl-6,7-dihydro-3H-imidazo[4,5-c]pyridine-5(4H)-carboxylate obtained from a process according to the third aspect of the invention.

In a fourth aspect, the present invention makes available a process for the preparation of (3S,4S)-tetrahydrofuran-3-yl 4-isopropyl-6,7-dihydro-3H-imidazo[4,5-c]pyridine-5(4H)-carboxylate and pharmaceutically acceptable salts thereof comprising the step of contacting (3S)-Tetrahydrofuran-3-yl 4-isopropyl-6,7-dihydro-3H-imidazo[4,5-c]pyridine-5(4H)-carboxylate (IV) with (R)-Mandelic acid (V):

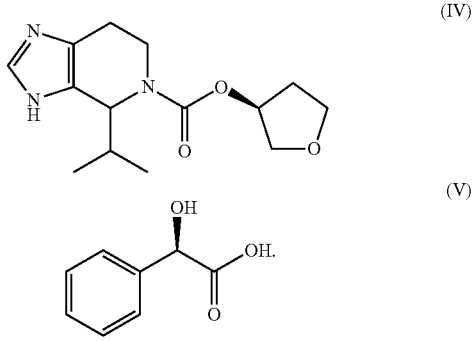

In an embodiment, the process comprises an additional crystallisation step, this additional step providing crystalline (3S,4S)-tetrahydrofuran-3-yl 4-isopropyl-6,7-dihydro-3H-imidazo[4,5-c]pyridine-5(4H)-carboxylate (R)-Mandelate (VI):

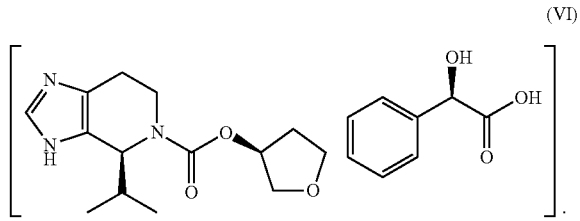

The crystallization step to provide (3S,4S)-tetrahydrofuran-3-yl 4-isopropyl-6,7-dihydro-3H-imidazo[4,5-c]pyridine-5(4H)-carboxylate (R)-Mandelate has a number of advantages. The crystallisation provides a surprisingly effective process for the removal of impurities, including stereoisomeric impurities. For example, the starting material for the crystallisation step is an approximately 1:1 mixture of: (3S,4R)-Tetrahydrofuran-3-yl 4-isopropyl-6,7-dihydro-3H-imidazo[4,5-c]pyridine-5(4H)-carboxylate (R)-Mandelate, and (3S,4S)-Tetrahydrofuran-3-yl 4-isopropyl-6,7-dihydro-3H-imidazo[4,5-c]pyridine-5(4H)-carboxylate (R)-Mandelate. The crystallisation step provides an effective method of separating the desired (3S,4S)-tetrahydrofuran-3-yl 4-isopropyl-6,7-dihydro-3H-imidazo[4,5-c]pyridine-5(4H)-carboxylate (R)-Mandelate from the undesired (3S,4R)-Tetrahydrofuran-3-yl 4-isopropyl-6,7-dihydro-3H-imidazo[4,5-c]pyridine-5(4H)-carboxylate (R)-Mandelate.

The claimed crystallisation method is a convenient, high yielding and scalable purification method, especially when compared to the chiral chromatographic methods used in the known synthesis. The skilled person knows that chromatography, especially chiral chromatography, on a large (i.e. kilogram) scale is undesirable due, at least, to the slow throughput, high cost and high volumes of solvent required.

The (3S,4S)-tetrahydrofuran-3-yl 4-isopropyl-6,7-dihydro-3H-imidazo[4,5-c]pyridine-5(4H)-carboxylate (R)-Mandelate crystals are easy to handle, thus facilitating preparation on a large scale.

In an embodiment, crystalline (3S,4S)-tetrahydrofuran-3-yl 4-isopropyl-6,7-dihydro-3H-imidazo[4,5-c]pyridine-5(4H)-carboxylate (R)-Mandelate is obtained in a yield of 20% or greater, such as 25% or greater, such as 30% or greater, such as 35% or greater.

The (3S,4S)-tetrahydrofuran-3-yl 4-isopropyl-6,7-dihydro-3H-imidazo[4,5-c]pyridine-5(4H)-carboxylate (R)-Mandelate crystals are obtained in a surprisingly high purity. In an embodiment, the crystalline (3S,4S)-tetrahydrofuran-3-yl 4-isopropyl-6,7-dihydro-3H-imidazo[4,5-c]pyridine-5(4H)-carboxylate (R)-Mandelate is obtained in a purity of 80% or greater, such as 90% or greater, such as 95% or greater.

The (3S,4S)-tetrahydrofuran-3-yl 4-isopropyl-6,7-dihydro-3H-imidazo[4,5-c]pyridine-5(4H)-carboxylate (R)-Mandelate crystals are obtained in a surprisingly high enantiomeric excess (e.e.). In an embodiment, the crystalline (3S,4S)-tetrahydrofuran-3-yl 4-isopropyl-6,7-dihydro-3H-imidazo[4,5-c]pyridine-5(4H)-carboxylate (R)-Mandelate is obtained in an enantiomeric excess (e.e.) of 95% or greater, such as 99% or greater, such as 99.9% or greater.

In an embodiment, the present invention makes available the novel compound (3S,4S)-tetrahydrofuran-3-yl 4-isopropyl-6,7-dihydro-3H-imidazo[4,5-c]pyridine-5(4H)-carboxylate (R)-Mandelate. In an embodiment the (3S,4S)-tetrahydrofuran-3-yl 4-isopropyl-6,7-dihydro-3H-imidazo[4,5-c]pyridine-5(4H)-carboxylate (R)-Mandelate is crystalline. In an embodiment, the (3S,4S)-tetrahydrofuran-3-yl 4-isopropyl-6,7-dihydro-3H-imidazo[4,5-c]pyridine-5(4H)-carboxylate (R)-Mandelate has an e.e. of 95% or greater, such as 99% or greater, such as 99.9% or greater. In an embodiment, the (3S,4S)-tetrahydrofuran-3-yl 4-isopropyl-6,7-dihydro-3H-imidazo[4,5-c]pyridine-5(4H)-carboxylate (R)-Mandelate has a purity of 80% or greater, such as 90% or greater, such as 95% or greater.

In an embodiment, the crystallisation step is effected by dissolving the (3S)-Tetrahydrofuran-3-yl 4-isopropyl-6,7-dihydro-3H-imidazo[4,5-c]pyridine-5(4H)-carboxylate (R)-Mandelate in warm (e.g. 60-80° C., or refluxing) acetonitrile, and then allowing the solution to cool to around room temperature whereupon the (3S,4S)-tetrahydrofuran-3-yl 4-isopropyl-6,7-dihydro-3H-imidazo[4,5-c]pyridine-5(4H)-carboxylate (R)-Mandelate crystals form. The skilled person understands that any suitable temperature(s) may be used, and any alternative solvent(s) may be used. Furthermore the skilled person understands that the crystallisation step may be repeated, for example to further improve the purity of the (3S,4S)-tetrahydrofuran-3-yl 4-isopropyl-6,7-dihydro-3H-imidazo[4,5-c]pyridine-5(4H)-carboxylate (R)-Mandelate salt.

In a fifth aspect, the present invention makes available a process for the preparation of (3S,4S)-tetrahydrofuran-3-yl 4-isopropyl-6,7-dihydro-3H-imidazo[4,5-c]pyridine-5(4H)-carboxylate and pharmaceutically acceptable salts thereof using (3S,4S)-tetrahydrofuran-3-yl 4-isopropyl-6,7-dihydro-3H-imidazo[4,5-c]pyridine-5(4H)-carboxylate (R)-Mandelate. In a related embodiment, the present invention makes available the use of (3S,4S)-tetrahydrofuran-3-yl 4-isopropyl-6,7-dihydro-3H-imidazo[4,5-c]pyridine-5(4H)-carboxylate (R)-Mandelate in a process for the preparation of (3S,4S)-tetrahydrofuran-3-yl 4-isopropyl-6,7-dihydro-3H-imidazo[4,5-c]pyridine-5(4H)-carboxylate and pharmaceutically acceptable salts thereof. In an embodiment, the pharmaceutically acceptable salt is the mesylate.

In a sixth aspect, the present invention makes available a process for the preparation of (3S,4S)-tetrahydrofuran-3-yl 4-isopropyl-6,7-dihydro-3H-imidazo[4,5-c]pyridine-5(4H)-carboxylate mesylate using (3S,4S)-tetrahydrofuran-3-yl 4-isopropyl-6,7-dihydro-3H-imidazo[4,5-c]pyridine-5(4H)-carboxylate (R)-Mandelate.

In an embodiment, the (R)-Mandelic acid is separated from the (3S,4S)-tetrahydrofuran-3-yl 4-isopropyl-6,7-dihydro-3H-imidazo[4,5-c]pyridine-5(4H)-carboxylate, and then the (3S,4S)-tetrahydrofuran-3-yl 4-isopropyl-6,7-dihydro-3H-imidazo[4,5-c]pyridine-5(4H)-carboxylate is converted to the mesylate salt, for example by contact with methanesulphonic acid or an equivalent. The (R)-Mandelic acid may be removed by any suitable technique known to the skilled person. In an embodiment the (R)-Mandelic acid is separated from the (3S,4S)-tetrahydrofuran-3-yl 4-isopropyl-6,7-dihydro-3H-imidazo[4,5-c]pyridine-5(4H)-carboxylate by treatment with an alkaline agent such as aqueous sodium hydrogen carbonate solution. As used herein, the term 'alkaline agent' means any compound or composition known to the skilled person suitable for removing (R)-Mandelic acid from the (3S,4S)-tetrahydrofuran-3-yl 4-isopropyl-6,7-dihydro-3H-imidazo[4,5-c]pyridine-5(4H)-carboxylate to as to liberate the free base of (3S,4S)-tetrahydrofuran-3-yl 4-isopropyl-6,7-dihydro-3H-imidazo[4,5-c]pyridine-5(4H)-carboxylate. Examples include, but are not limited to, sodium hydrogen carbonate and basic ion exchange resin.

In an embodiment, the resultant (3S,4S)-tetrahydrofuran-3-yl 4-isopropyl-6,7-dihydro-3H-imidazo[4,5-c]pyridine-5(4H)-carboxylate mesylate is isolated, and then further purified by an additional crystallisation step. In an embodiment, the crystallisation step is performed by dissolving the (3S,4S)-tetrahydrofuran-3-yl 4-isopropyl-6,7-dihydro-3H-imidazo[4,5-c]pyridine-5(4H)-carboxylate mesylate in a warm (e.g. from 40 to 70° C.) mixture of methylethyl ketone and water, and then allowing the mixture to cool to around room temperature. The high purity and e.e. of the (3S,4S)-tetrahydrofuran-3-yl 4-isopropyl-6,7-dihydro-3H-imidazo[4,5-c]pyridine-5(4H)-carboxylate (R)-Mandelate starting material assists in making available crystalline (3S,4S)-tetrahydrofuran-3-yl 4-isopropyl-6,7-dihydro-3H-imidazo[4,5-c]pyridine-5(4H)-carboxylate mesylate having a high purity and e.e.

In an embodiment, the crystalline (3S,4S)-tetrahydrofuran-3-yl 4-isopropyl-6,7-dihydro-3H-imidazo[4,5-c]pyridine-5(4H)-carboxylate mesylate is obtained in a purity of 95% or greater, such as 99% or greater, such as 99.5% or greater, such as 99.9% or greater.

In an embodiment, the crystalline (3S,4S)-tetrahydrofuran-3-yl 4-isopropyl-6,7-dihydro-3H-imidazo[4,5-c]pyridine-5(4H)-carboxylate mesylate is obtained in an e.e. of 95% or greater, such as 99% or greater, such as 99.5% or greater, such as 99.9% or greater.

Terminology

As used herein the term "pharmaceutically acceptable salt" includes base addition, acid addition and quaternary salts. (3S,4S)-tetrahydrofuran-3-yl 4-isopropyl-6,7-dihydro-3H-imidazo[4,5-c]pyridine-5(4H)-carboxylate can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic and p-toluene sulphonic acids and the like. For a review on suitable salts, see *Handbook of Pharmaceutical Salts: Properties, Selection, and Use* by Stahl and Wermuth (Wiley-VCH, Weinheim, Germany, 2002).

In common with many organic compounds useful in medicine, at least some of the compounds of the invention are expected to be recoverable as crystalline hydrates and solvates. Such hydrates and solvates are of course merely specific physico-chemical forms of the active compounds of the invention and therefore form part of the invention. Any unqualified reference herein to (3S,4S)-tetrahydrofuran-3-yl 4-isopropyl-6,7-dihydro-3H-imidazo[4,5-c]pyridine-5(4H)-carboxylate is to be construed as a reference to that compound, irrespective of whether it is or is not in the form of a hydrate or solvate. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

The compounds with which the invention is concerned may be prepared for administration by any route consistent with their pharmacokinetic properties. The orally administrable compositions may be in the form of tablets, capsules, powders, granules, lozenges, liquid or gel preparations. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents. Other particular formulations for oral administration include chewing gums, and suckable lozenges and lollipops, containing the compound of the invention.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia. Methods of delivery via sustained release patches for application to the skin are also known in the art.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

The active ingredient may also be formulated for inhalation, for example as a nasal spray, or dry powder or aerosol inhalers. For delivery by inhalation, the active compound is preferably in the form of microparticles. They may be prepared by a variety of techniques, including spray-drying, freeze-drying and micronisation. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

Compounds of the invention may be administered together with other classes of pharmaceutically active drugs.

Preparation of Compounds of the Invention

The processes, uses, reactions and compounds of the present invention may in particular be illuminated by the following Schemes.

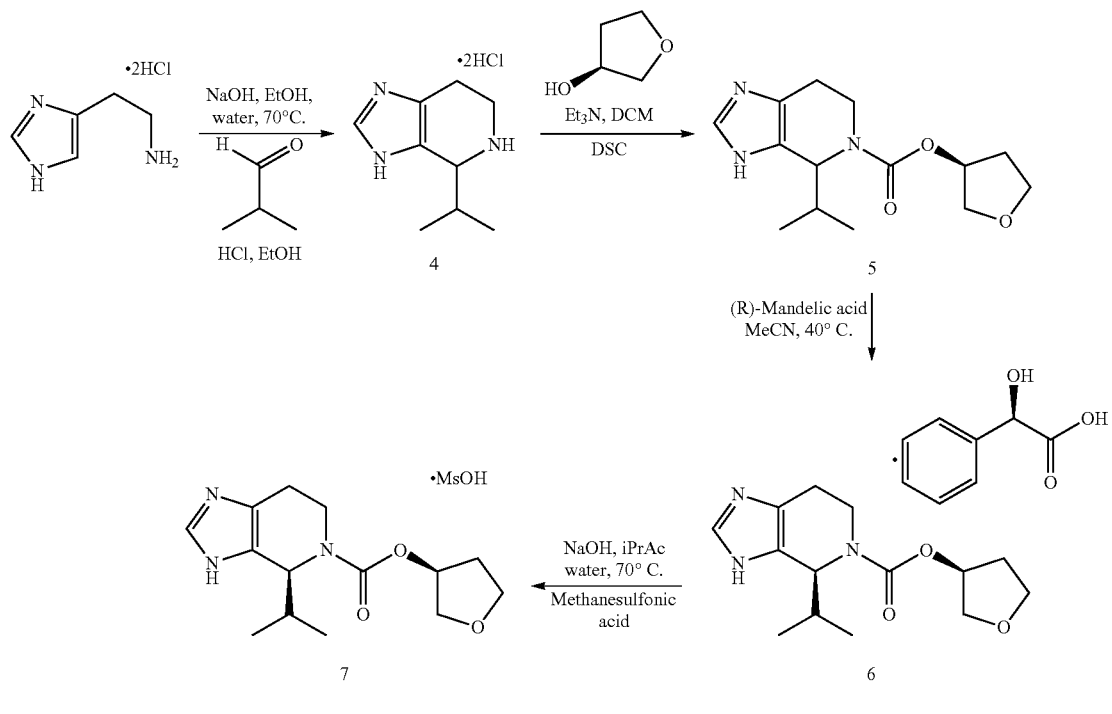

Scheme 2

General synthetic route for preparation of (3S,4S)-tetrahydrofuran-3-yl 4-isopropyl-6,7-dihydro-3H-imidazo[4,5-c]pyridine-5(4H)-carboxylate, and the mesylate salt thereof.

The following abbreviations have been used:
br broad
d doublet
DCM dichloromethane
dd double doublet
DIPEA diisopropylethylamine
DMSO dimethyl sulfoxide
DSC N,N-disuccinimidyl carbonate
Et₃N triethylamine
EtOH ethanol
HPLC high performance liquid chromatography
iPrAC isopropyl acetate
LCMS liquid chromatography mass spectrometry
m multiplet
M molar
Me methyl
MeCN acetonitrile
MeOH methanol
MsOH methanesulfonic acid
NMR nuclear magnetic resonance
Ph phenyl
s singlet
THF tetrahydrofuran

EXAMPLES AND INTERMEDIATE COMPOUNDS

Experimental Methods

Reactions were conducted at room temperature unless otherwise specified. Compound analysis was performed by HPLC/LCMS using a Waters XSelect CSH system using a C18 column (150×4.6 mm, 3.5 um, 1.5 mM ammonium bicarbonate in water pH10.7 in 50 mM ammonium bicarbonate in water/MeCN 25/75 v/v, 220 nM detection, 25° C., 1 mL/min). Chiral HPLC was performed using a Daicel Chiralpak AD-H column (250×4.6 mm, 5 um, n-heptane/propan-2-ol/diethylamine 90/20/0.02 v/v/v, 220 nm detection, 50° C., 1 mL/min). 1H NMR was performed on a Bruker 400 MHz machine. The compounds prepared were named using IUPAC nomenclature.

Preparation of 4-Isopropyl-4,5,6,7-tetrahydro-3H-imidazo[4,5-c]pyridine Dihydrochloride (4)

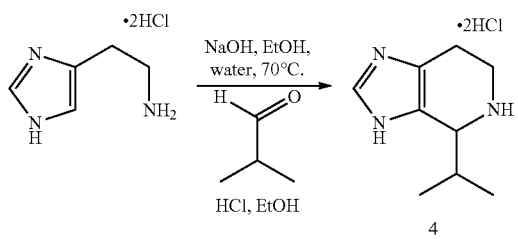

Histamine dihydrochloride (130 kg; 706 moles) was stirred in water (13.1 L) and ethanol (353 kg). The yellow solution was cooled to 0-5° C. Sodium hydroxide pellets (57.4 kg; 1435 mole) were added to the solution over five hours, maintaining the temperature at below 10° C. The reaction mixture was heated to 20-26° C. for one hour and then to reflux temperature. Isobutyraldehyde (61.4 kg; 852 mole) was added over 2.5 hours maintaining the temperature at 76° C., and the mixture heated at this temperature for 5.5 hours. The mixture was cooled to 0-5° C., stirred for 2 hours and filtered. The solid was washed with cold ethanol (430 kg). The filtrate was distilled to low volume (390 L) and cooled to 18-23° C. Acetyl chloride (170 kg; 2166 mole) was added to ethanol (523 kg) at below 20° C. over 1 hour. The solution was stirred at 18-20° C. for a further hour before cooling to 0-5° C. The reaction product ethanol solution was added to this solution over one hour at below 25° C. The mixture was stirred at 18-23° C. for five hours before filtering. The solid was washed with cold ethanol (107 kg), collected and dried in vacuo at 40° C. 4-Isopropyl-4,5,6,7-tetrahydro-3H-imidazo[4,5-c]pyridine dihydrochloride (4, 161 kg; 96%) was obtained as a white, crystalline solid, 99.6% pure (HPLC). 1H NMR conforms to reference standard (1H NMR $\delta_H$ (d4-MeOH) 15.10 (2H, br s, NHCHNH), 10.40 (1H, br s, NH$_2$), 9.40 (1H, br s, NH$_2$), 9.10 (1H, s, NHCHNH), 4.60-4.52 (1H, br m), 3.57-3.48 (1H, m), 3.32-3.22 (1H, br m), 3.13-3.02 (1H, br m), 2.97-2.87 (1H, br m), 2.67 (1H, m, Me$_2$CH), 1.10 (3H, d, Me) and 0.95 (3H, d, Me)).

Preparation of (3S)-Tetrahydrofuran-3-yl 4-isopropyl-6,7-dihydro-3H-imidazo[4,5-c]pyridine-5(4H)-carboxylate (5)

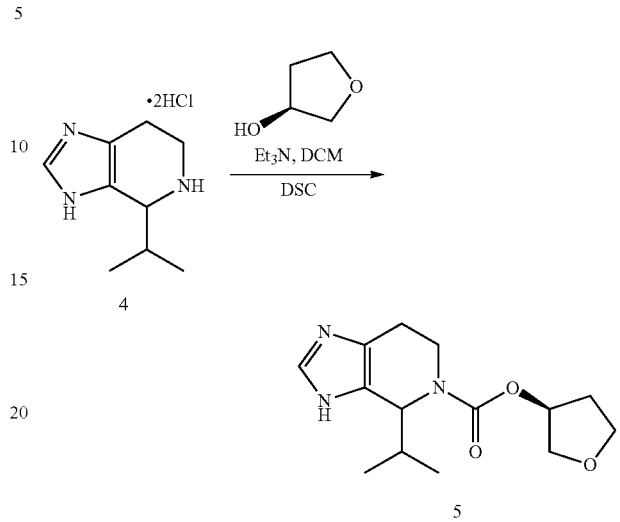

N,N-Disuccinimidyl carbonate (94.8 kg; 370 mole) and triethylamine (38.6 kg; 381 mole) were stirred in dichloromethane (239 kg). (S)-(+)-3-Hydroxytetrahydrofuran (31.8 kg; 361 mole) was added to the mixture at below 28° C. The mixture was stirred at 22-28° C. for 26 hr. 4-Isopropyl-4,5,6,7-tetrahydro-3H-imidazo[4,5-c]pyridine dihydrochloride (4, 79.0 kg; 332 mole) was added to the reaction mixture, followed by triethylamine (81.2 kg; 802 mole), maintaining the temperature at 27-33° C. The reaction mixture was then stirred in this temperature for ten hours. 4M Hydrochloric acid (235 L) was added to the reaction mixture to adjust the pH to between pH 1.0 and pH 2.0, maintaining the temperature at <25° C. and the resultant mixture was stirred for 30-40 min. The layers were separated and the organic layer re-extracted twice with 20% w/w aqueous sodium chloride solution (185 L each). The aqueous layers were combined, pH adjusted to pH 9.5-10.5 with 4M sodium hydroxide solution (506 L) and extracted with methylene chloride (3×375 L). The organic extracts were combined and washed with 20% w/w aqueous sodium chloride solution (230 L). The organic layer was concentrated to low volume (237 L) and solvent switched into acetonitrile. (3S)-Tetrahydrofuran-3-yl 4-isopropyl-6,7-dihydro-3H-imidazo[4,5-c]pyridine-5(4H)-carboxylate (5, 72.2 kg; 78%) was isolated as a solution in acetonitrile, 85.8% pure (HPLC).

Preparation of R-(−)-Mandelic Acid Salt of (3S, 4S)-tetrahydrofuran-3-yl 4-isopropyl-6,7-dihydro-3H-imidazo[4,5-c]pyridine-5(4H)-carboxylate (6)

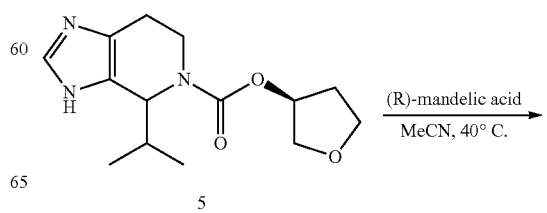

-continued

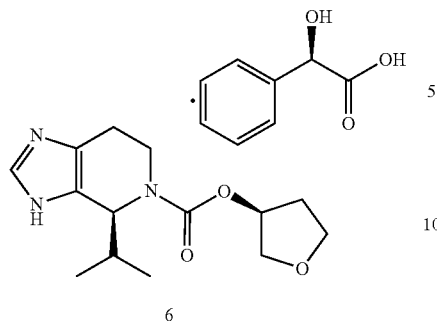

6

R-(−)-Mandelic acid (65.6 kg; 431 mole) was added to a solution of (3S)-tetrahydrofuran-3-yl 4-isopropyl-6,7-dihydro-3H-imidazo[4,5-c]pyridine-5(4H)-carboxylate in acetonitrile (5, 122 kg in 384 kg; 436 mole) and acetonitrile (629 kg). The mixture was stirred at 24° C. until a solution was obtained, heated to 40° C. and held at this temperature for four hours to ensure crystallisation. The mixture was then stirred at 20-25° C. for 28 hours, before filtering the solid. The solid was washed with acetonitrile (48.2 kg) and sucked dry on the filter for 6 hours.

The damp solid (95.4 kg) was stirred in acetonitrile (1008 kg) and heated to reflux temperature to dissolve the solid. The solution was cooled to 60° C. over 3.5 hours to ensure crystallisation then cooled to 24° C. and stirred for 6 hours before filtering. The solid was washed with acetonitrile (48.6 kg) and dried in vacuo at 40° C. for 6 hours. The R-(−)-mandelic acid salt of tetrahydrofuran-3-yl 4-isopropyl-6,7-dihydro-3H-imidazo[4,5-c]pyridine-5(4H)-carboxylate (6, 72.7 kg; 39%) was isolated as a white crystalline solid, 96.5% pure (HPLC), 99.9% e.e. (Chiral HPLC). 1H NMR conforms to reference standard (1H NMR $\delta_H$ (d4-MeOH) 7.85 (1H, d, NHC$\underline{H}$NH), 7.48-7.21 (5H, m, P$\underline{h}$), 5.24 (1H, br s, OC$\underline{H}$), 5.05 (1H, s, C$\underline{H}$OH), 4.95 (1H, s, CHO$\underline{H}$), 4.86-4.72 (1H, m, NC$\underline{H}$), 4.44-4.29 (1H, m, NC$\underline{H}_2$), 3.95-3.75 (4H, m, C$\underline{H}_2$OC$\underline{H}_2$), 3.35-3.20 (1H, br m, NC$\underline{H}_2$), 2.78-2.60 (2H, br m, NCH$_2$C$\underline{H}_2$), 2.27-1.99 (3H, br m, OCH$_2$C$\underline{H}_2$ and Me$_2$C$\underline{H}$), 1.11 (3H, d, $\underline{Me}$) and 0.97 (3H, d, $\underline{Me}$)).

Preparation of Methanesulfonic Acid Salt of (3S, 4S)-tetrahydrofuran-3-yl 4-isopropyl-6,7-dihydro-3H-imidazo[4,5-c]pyridine-5(4H)-carboxylate (7, crude)

6 →(NaOH, iPrAc, water, 70° C. / Methanesulfonic acid)→ 7

Tetrahydrofuran-3-yl 4-isopropyl-6,7-dihydro-3H-imidazo[4,5-c]pyridine-5(4H)-carboxylate mandelate salt (6, 45.2 kg; 105 mole) was stirred with 8% aqueous sodium hydrogen carbonate solution (300 L) and isopropyl acetate (317 kg) at 20-25° C. to give the aqueous layer at pH 8. The aqueous layer was re-extracted twice with isopropyl acetate (315 L each). The combined organic extracts were washed with 8% aqueous sodium hydrogen carbonate solution (4×300 L). The aqueous washes were combined and extracted with isopropyl acetate (317 L). The organic layers were combined and concentrated under reduced pressure to low volume (181 L). The solution was heated to 70° C. and a solution of methanesulfonic acid (9.94 kg; 103 mole) in isopropyl acetate (13.2 kg) added and the mixture heated at 70° C. for a further 3 hours. The solution was cooled to 40° C. over 2 hours to ensure crystallisation then cooled to 17° C. over 90 minutes and held at this temperature for 2 hours before filtering. The solid was washed with isopropyl acetate (72 kg) and dried in vacuo at 60° C. for 6 hours. Crude methanesulfonic acid salt of (3S,4S)-tetrahydrofuran-3-yl 4-isopropyl-6,7-dihydro-3H-imidazo[4,5-c]pyridine-5(4H)-carboxylate (7, 34.1 kg; 87%) was isolated as a white crystalline solid, 99.9% pure (HPLC), 100% e.e. (Chiral HPLC).

Recrystallisation of Methanesulfonic Acid Salt of (3S,4S)-tetrahydrofuran-3-yl 4-isopropyl-6,7-dihydro-3H-imidazo[4,5-c]pyridine-5(4H)-carboxylate (7)

Crude methanesulfonic acid salt of (3S,4S)-tetrahydrofuran-3-yl 4-isopropyl-6,7-dihydro-3H-imidazo[4,5-c]pyridine-5(4H)-carboxylate (7, 102 kg; 272 mole) was dissolved in methylethyl ketone (663 kg) and water (18.3 kg) at 70° C. and cooled over 40° C. over 100 minutes, ensuring crystallisation. The mixture was cooled to 20° C. over 1 hour and held at this temperature for a further 3 hours before filtering. The solid was washed with methylethyl ketone (163 kg) and dried in vacuo at 40° C. for 8 hours. Methanesulfonic acid salt of (3S,4S)-tetrahydrofuran-3-yl 4-isopropyl-6,7-dihydro-3H-imidazo[4,5-c]pyridine-5(4H)-carboxylate (7, 89.9 kg; 88%) was isolated as a white crystalline solid, 99.9% pure (HPLC), 100% e.e. (Chiral HPLC). 1H NMR conforms to reference standard (1H NMR $\delta_H$ (d6-DMSO) 14.30 (2H, br s, N$\underline{H}$CHN$\underline{H}$), 9.00 (1H, s, NHC$\underline{H}$NH), 5.15 (1H, br s, OC$\underline{H}$), 4.83 (1H, dd, NC$\underline{H}$), 4.30, (1H, dd, NC$\underline{H}_2$), 3.87-3.65 (4H, m, C$\underline{H}_2$OC$\underline{H}_2$), 3.30-3.13 (1H, br m, NC$\underline{H}_2$), 2.78-2.62 (2H, m, NCH$_2$C$\underline{H}_2$), 2.35 (3H, s, SO$_2$$\underline{Me}$), 2.18-1.87 (3H, br m, OCH$_2$C$\underline{H}_2$ and Me$_2$C$\underline{H}$), 1.03 (3H, d, $\underline{Me}$) and 0.90 (3H, d, $\underline{Me}$)).

The invention claimed is:
1. A process for the preparation of (3S,4S)-tetrahydrofuran-3-yl 4-isopropyl-6,7-dihydro-3H-imidazo[4,5-c]pyridine-5(4H)-carboxylate, or a pharmaceutically acceptable salt thereof, comprising:

contacting (3S)-Tetrahydrofuran-3-yl 4-isopropyl-6, 7-dihydro-3H-imidazo[4,5-c]pyridine-5(4H)-carboxylate (IV) with (R)-Mandelic acid (V):

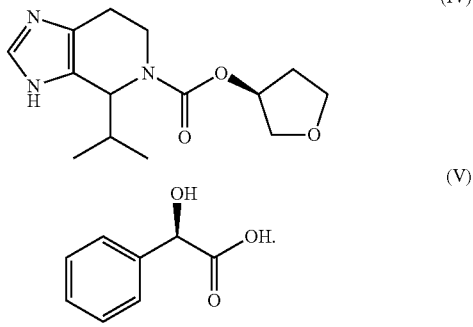

(IV)

(V)

2. The process according to claim 1, further comprising an additional crystallisation to obtain crystalline (3 S,4S)-tetrahydrofuran-3-yl 4-isopropyl-6,7-dihydro-3H-imidazo[4,5-c]pyridine-5(4H)-carboxylate (R)-Mandelate (VI):

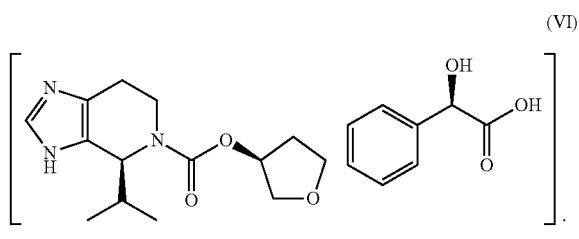

(VI)

3. The process according to claim 2, wherein the (3S,4S)-tetrahydrofuran-3-yl 4-isopropyl-6, 7-dihydro-3H-imidazo[4,5-c]pyridine-5 (4H)-carboxylate (R)-Mandelate is obtained in
(i) a yield of 20% or greater,
(ii) a purity of 80% or greater, and/or (iii) an enantiomeric excess (e.e.) of 95% or greater.

4. A compound comprising (3S,4S)-tetrahydrofuran-3-yl 4-isopropyl-6,7-dihydro-3H-imidazo[4,5-c]pyridine-5(4H)-carboxylate (R)-mandelate.

5. The compound according to claim 4, wherein the (3 S,4S)-tetrahydrofuran-3-yl 4-isopropyl-6, 7-dihydro-3H-imidazo[4,5-c]pyridine-5 (4H)-carboxylate (R)-mandelate has
(i) an e.e. of 95% or greater, and/or
(ii) a purity of 80% or greater.

6. A process for the preparation of (3S,4S)-tetrahydrofuran-3-yl 4-isopropyl-6, 7-dihydro-3H-imidazo[4,5-c]pyridine-5 (4H)-carboxylate and pharmaceutically acceptable salts thereof using 4-Isopropyl-4,5,6,7-tetrahydro-3H-imidazo[4,5-c]pyridine dihydrochloride.

7. A process for the preparation of (3S,4S)-tetrahydrofuran-3-yl 4-isopropyl-6, 7-dihydro-3H-imidazo[4,5-c]pyridine-5 (4H)-carboxylate and pharmaceutically acceptable salts thereof using (3S,4S)-tetrahydrofuran-3-yl 4-isopropyl-6,7-dihydro-3H-imidazo[4,5-c]pyridine-5(4H)-carboxylate(R)-mandelate.

8. The process according to claim 1, wherein the pharmaceutically acceptable salt is the mesylate salt.

9. A process for the preparation of (3S,4S)-tetrahydrofuran-3-yl 4-isopropyl-6,7-dihydro-3H-imidazo[4,5-c]pyridine-5 (4H)-carboxylate mesylate from (3 S,4S)-tetrahydrofuran-3-yl 4-isopropyl-6,7-dihydro-3H-imidazo[4,5-c]pyridine-5(4H)-carboxylate (R)-mandelate.

10. A process according to claim 9, wherein
(a) the (R)-mandelic acid is separated from the (3S,4S)-tetrahydrofuran-3-yl 4-isopropyl-6,7-dihydro-3H-imidazo[4,5-c]pyridine-5(4H)-carboxylate by treatment with an alkaline agent, and then
(b) the (3 S,4S)-tetrahydrofuran-3-yl 4-isopropyl-6, 7-dihydro-3H-imidazo[4,5-c]pyridine-5(4H)-carboxylate is treated with methanesulphonic acid,
optionally comprising a crystallization to provide crystalline (3S,4S)-tetrahydrofuran-3-yl 4-isopropyl-6, 7-dihydro-3H-imidazo[4,5-c]pyridine-5(4H)-carboxylate mesylate, wherein the (3 S,4S)-tetrahydrofuran-3-yl 4-isopropyl-6, 7-dihydro-3H-imidazo[4,5-c]pyridine-5(4H)-carboxylate mesylate is obtained in a purity of 95% or greater; and/or
an e.e. of 95% or greater.

11. The process according to claim 1, wherein the (3 S)-tetrahydrofuran-3-yl 4-isopropyl-6, 7-dihydro-3H-imidazo[4, 5-c]pyridine-5 (4H)-carboxylate(IV) is formed by coupling 4-isopropyl-4,5,6,7-tetrahydro-3H-imidazo[4,5-c]pyridine (II) or a dihydrochloride salt thereof and (S)-(+)-3-hydroxytetrahydrofuran (III) using a coupling agent to form (3S)-tetrahydrofuran-3-yl 4-isopropyl-6,7-dihydro-3H-imidazo[4, 5-c]pyridine-5(4H)-carboxylate(IV):

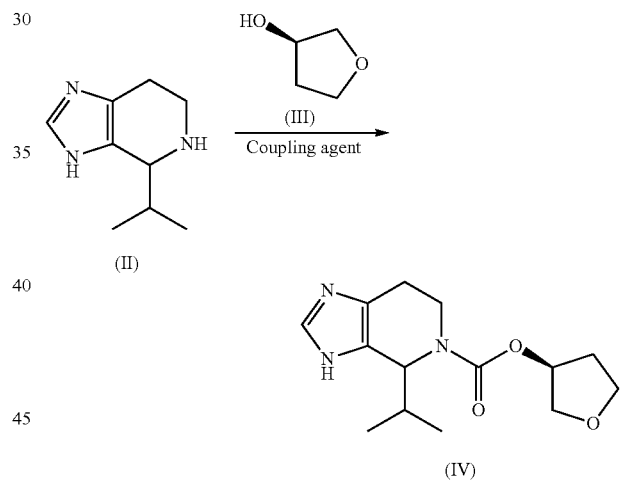

wherein the coupling agent is N,N-disuccinimidyl carbonate.

12. The process according to claim 11, wherein the process comprises:
reacting histamine (I) with isobutyraldehyde to form 4-isopropyl-4,5,6,7-tetrahydro-3H-imidazo[4,5-c]pyridine (II) or a dihydrochloride salt thereof

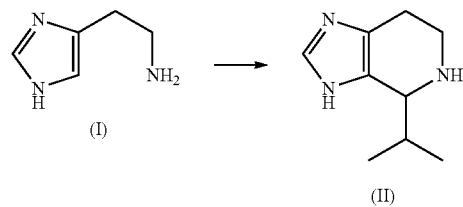

wherein the reaction to form 4-isopropyl-4,5,6,7-tetrahydro-3H-imidazo[4,5-c]pyridine (II) is maintained at a temperature of from 50 to 100° C. for a period of from 1 to 12 hours.

13. The process according to claim 12, wherein the reaction further comprises a solvent, and the solvent comprises ethanol, and/or the reaction is maintained at a temperature of refluxing ethanol,
optionally, wherein in the process, the 4-isopropyl-4,5,6,7-tetrahydro-3H-imidazo[4,5-c]pyridine dihydrochloride is isolated in
(i) a yield of 80% or greater; and/or
(ii) a purity of 95% or greater.

14. The process according to claim 11, wherein the coupling
(i) is carried out in a solvent, and the solvent comprises dichloromethane; and/or
(ii) the reaction step comprises trimethylamine,
optionally wherein (3 S)-tetrahydrofuran-3-yl 4-isopropyl-6,7-dihydro-3H-imidazo[4,5-c]pyridine-5(4H)-carboxylate is obtained in a yield of 70% or greater and/or a purity of 80% or greater.

15. The process according to claim 3, wherein the (3 S,4S)-tetrahydrofuran-3-yl 4-isopropyl-6,7-dihydro-3H-imidazo[4,5-c]pyridine-5(4H)-carboxylate (R)-Mandelate is obtained in
(i) a yield of 30% or greater,
(ii) a purity of 95% or greater, and/or
(iii) an enantiomeric excess (e.e.) of 99.9% or greater.

16. The compound according to claim 5, wherein the (3S,4S)-tetrahydrofuran-3-yl 4-isopropyl-6, 7-dihydro-3H-imidazo[4, 5-c]pyridine-5 (4H)-carboxylate(R)-mandelate has
(i) an e.e. of 99.9% or greater, and/or
(ii) a purity of 95% or greater.

17. The process according to claim 10, wherein
the alkaline agent is an aqueous sodium hydrogen carbonate, and
optionally comprising a crystallization to provide crystalline (3S,4S)-tetrahydrofuran-3-yl 4-isopropyl-6,7-dihydro-3H-imidazo[4,5-c]pyridine-5(4H)-carboxylate mesylate, wherein the (3 S,4S)-tetrahydrofuran-3-yl 4-isopropyl-6,7-dihydro-3H-imidazo[4,5-c]pyridine-5 (4H)-carboxylate mesylate is obtained in a purity of 99.9% or greater; and/or
an e.e. of 99.9% or greater.

18. The process according to claim 12, wherein the 4-isopropyl-4,5,6,7-tetrahydro-3H-imidazo[4,5-c]pyridine (II) is the dihydrochloride, and optionally wherein the dihydrochloride is isolated.

19. The process according to claim 12, wherein the reaction to form 4-isopropyl-4,5,6,7-tetrahydro-3H-imidazo[4,5-c]pyridine (II) is maintained at a temperature of from 60 to 80° C. for a period of from 1 to 12 hours.

20. The process according to claim 12, wherein the reaction to form 4-isopropyl-4,5,6,7-tetrahydro-3H-imidazo[4,5-c]pyridine (II) is maintained at a temperature of from 50 to 100° C. for a period of from 5 to 7 hours.

* * * * *